(12) United States Patent
Tsujii et al.

(10) Patent No.: US 7,754,887 B2
(45) Date of Patent: Jul. 13, 2010

(54) PROCESS FOR PRODUCTION OF SULFOXIDE DERIVATIVES OR SALTS THEREOF IN THE AMORPHOUS STATE

(75) Inventors: Masahiko Tsujii, Omigawa-machi (JP); Yukio Morita, Fukaya (JP)

(73) Assignee: EISAI R&D Management Co., Ltd., Tokyo (JP)

( * ) Notice: Subject to any disclaimer, the term of this patent is extended or adjusted under 35 U.S.C. 154(b) by 273 days.

(21) Appl. No.: 11/939,418

(22) Filed: Nov. 13, 2007

(65) Prior Publication Data

US 2008/0214828 A1 Sep. 4, 2008

Related U.S. Application Data (63) Continuation of application No. 10/546,994, filed as application No. PCT/JP2004/003525 on Mar. 17, 2004, now abandoned.

(30) Foreign Application Priority Data

Mar. 24, 2003 (JP) ............................. 2003-081261

(51) Int. Cl.
C07D 401/12 (2006.01)
(52) U.S. Cl. .................................... 546/273.7
(58) Field of Classification Search ............... 546/273.7
See application file for complete search history.

(56) References Cited

U.S. PATENT DOCUMENTS

| 4,738,974 | A | 4/1988 | Brandstrom |
| 5,045,552 | A | 9/1991 | Souda et al. |
| 6,162,816 | A | 12/2000 | Bohlin et al. |
| 6,180,652 | B1 | 1/2001 | Tsujii et al. |
| 6,713,495 | B1 | 3/2004 | Sherman et al. |
| 2003/0045724 | A1 | 3/2003 | Fujishima et al. |
| 2003/0181487 | A1 | 9/2003 | Kamiyama et al. |

FOREIGN PATENT DOCUMENTS

| EP | 1 552 833 A1 | 7/2005 |
| JP | 59-167587 A | 9/1984 |
| JP | 1-006270 A | 1/1989 |
| JP | 8-176113 A | 7/1996 |
| JP | 2000-143659 A | 5/2000 |
| JP | 2001-122783 A | 5/2001 |
| JP | 2001-507025 A | 5/2001 |
| JP | 2002-114779 A | 4/2002 |
| WO | WO-01/87831 A2 | 11/2001 |
| WO | WO-2004/002982 A2 | 1/2004 |
| WO | WO-2004/056804 A2 | 7/2004 |

OTHER PUBLICATIONS

Vrecer, "Investigation of glassy state of two novel benzimidazole derivatives," Farmacevtski Vestnik, 50 (Pos. Stev.), 1999, 347-348.
Threlfall, "Analysis of Organic Polymorphs," Analyst, 1995, 120, pp. 2435-2460.
Vippagunta et al., "Crystalline solids", Advanced Drug Delivery Reviews 48 (2001), pp. 3-26.

*Primary Examiner*—Patricia L Morris
(74) *Attorney, Agent, or Firm*—Birch, Stewart, Kolasch & Birch, LLP (57) ABSTRACT

Process for producing sulfoxide derivatives or salts thereof in the amorphous state, characterized by heat-drying solvated crystals of a sulfoxide derivative or a salt thereof represented by the general formula (I):

wherein $R_1$ represents a hydrogen atom, a methoxy group, or a difluoromethoxy group; $R_2$ represents a methyl group or a methoxy group; $R_3$ represents a 3-methoxypropoxy group, a methoxy group, or a 2,2,2-trifluoroethoxy group; $R_4$ represents a hydrogen atom or a methoxy group; and B represents a hydrogen atom, an alkali metal or ½ alkaline earth metal.

7 Claims, 9 Drawing Sheets

PROCESS FOR PRODUCTION OF SULFOXIDE DERIVATIVES OR SALTS THEREOF IN THE AMORPHOUS STATE

CROSS-REFERENCE TO RELATED APPLICATIONS

This application is a continuation of application Ser. No. 10/546,994, filed Aug. 26, 2005 now abandoned. Ser. No. 10/546,994 is the U.S. national phase of international application PCT/JP2004/003525, filed Mar. 17, 2004. Priority thereto is claimed under 35 U.S.C. §120. Priority is claimed under 35 U.S.C. §119 to Japanese patent application 2003-081261, filed Mar. 24, 2003. The foregoing applications are incorporated by reference herein.

TECHNICAL FIELD OF THE INVENTION

The present invention relates to a method of effectively preparing an amorphous substance of sulfoxide derivative or the salt thereof, wherein the substance is useful as medical drugs such as inhibitors of gastric acid secretion and anti-ulcer agents, and said method comprises heat-drying a solvated crystal of sulfoxide derivative or the salt thereof.

BACKGROUND OF THE INVENTION

In the prior method of preparing one of sulfoxide derivative or the salt thereof, 2-[[4-(3-methoxypropoxy)-3-methylpyridine-2-yl]methylsulfinyl]-1H-benzimidazole sodium salt (general designation: Rabeprazole sodium salt) represented by the formula (I) wherein $R_1$ represents a hydrogen atom, a methoxy group or a difluoromethoxy group; $R_2$ represents a methyl group or a methoxy group; $R_3$ represents a 3-methoxypropoxy group, a methoxy group or a 2,2,2-trifluoroethoxy group; $R_4$ represents a hydrogen atom or a methyl group; respectively, and B represents a hydrogen atom, an alkaline metal or ½ alkaline earth metal, 2-[[4-(3-methoxypropoxy)-3-methylpyridine-2-yl]-methylsulfinyl]1H-benzimidazole (general designation: Rabeprazole) had been dissolved in aqueous sodium hydroxide solution and then freeze-dried to obtain the amorphous substance thereof (see Patent Publication 1), or an acetone complex of 2-[[4-(3-methoxypropoxy)-3-methylpyridine-2-yl]-methylsulfinyl]-1H-benzimidazole sodium salt had been freeze-dried to obtain the amorphous substance thereof (see Patent Publication 2).

The method of preparing an amorphous substance by freeze-dry is general means for obtaining drugs, as a solid, mainly unstable protein drugs and antibiotics.

However, such methods have serious problems in light of preparing time, cost or environmental protection, for example, 1) the production scale is restricted due to plant-capacity or -ability and a large scale plant for freeze-dry exclusive use is required in case of industrial scale production, and 2) additional drying step of removing water is required after freeze-dry in case of drugs which are unstable to water.

In addition, it has been, known to be difficult to make the particle diameter of the amorphous substance obtained by freeze-dry the same size. In particular, in case of compounds such as Rabeprazole, whose water-controlling is important due to their deliquescence, there was a problem, that is, it is difficult to add steps of grinding and screening.

[Patent Publication 1]

U.S. Pat. No. 5,045,552

[Patent Publication 2]

U.S. Pat. No. 6,180,652

DISCLOSURE OF THE INVENTION

In light of the above-mentioned things, an object of the present invention is to provide a method of effectively preparing an amorphous substance of sulfoxide derivative (I) or the salt thereof in industrial scale, said method overcoming the above-mentioned problem caused in, the freeze-dry method.

The inventors have assiduously conducted investigations in light of the above-mentioned things. They have consequently found that a colorless amorphous substance of sulfoxide derivative (I) or the salt thereof is successively, stably obtained in industrial scale by subjecting a solvated crystal of sulfoxide derivative (I) or the salt thereof to heat-drying at high temperature which defies the prior common sense, and that said drying method provides the amorphous substance of sulfoxide derivative (I) or the salt thereof, whose particle diameter is in a uniformly arranged condition. This finding has led to the completion of the present invention.

The present invention provides the following <1> to <32>:

<1> A method of preparing an amorphous substance of sulfoxide derivative (I) or the salt thereof, which comprises heat-drying an solvated crystal of sulfoxide derivative represented by the following formula (I) or the salt thereof wherein $R_1$ represents a hydrogen atom, a methoxy group or a difluoromethoxy group; $R_2$ represents a methyl group or a, methoxy group; $R_3$ represents a 3-methoxypropoxy group, a methoxy group or a 2,2,2-trifluoroethoxy group; $R_4$ represents a hydrogen atom or a methyl group; respectively, and B represents a hydrogen atom, an alkaline metal or ½ alkaline earth metal.

<2> The method according to the above item <1>, wherein the solvated crystal of sulfoxide derivative (I) or the salt thereof is heat-dried under reduced pressure.

<3> The method according to the above item. <1> or <2>, wherein the solvated crystal of sulfoxide derivative (I) or the salt thereof is heat-dried with moist gas.

<4> The method according to the above item <1>, wherein the solvated crystal of sulfoxide derivative (I) or the salt thereof is heat-dried in an inert medium.

<5> The method according to any one of the above items <1> to <4>, wherein the sulfoxide derivative is 2-[[4-(3-metoxypropoxy)-3-methylpyridine-2-yl]-methylsulfinyl]-1H-benzimidazole, 2-[[4-(2,2,2-trifluoroethoxy)-3-methylpyridine-2-yl]methylsulfinyl]-1H-benzimidazole, 5-methoxy-2-[(4-methoxy-3,5-dimethyl-2-pyridyl)methylsulfinyl]-1H-benzimidazole or 5-difluoromethoxy-2-[(4,5-dimethoxy-2-pyridyl)methylsulfinyl]-1H-benzimidazole.

<6> A method of preparing an amorphous substance of 2-[[4-(3-methoxypropoxy)-3-methylpyridine-2-yl]methylsulfinyl]-1H-benzimidazole sodium salt, comprising heat-drying an acetone complex of 2-[[4-(3-methoxypropoxy)-3-methylpyridine-2-yl]methylsulfinyl]-1H-benzimidazole sodium salt or an acetonitrile complex of 2-[[4-(3-methoxypropoxy)-3-methylpyridine-2-yl]methylsulfinyl]-1H-benzimidazole sodium salt under reduced pressure.

<7> A method of preparing an amorphous substance of 2-[[4-(3-methoxypropoxy)-3-methylpyridine-2-yl]methylsulfinyl]-1H-benzimidazole sodium salt, which comprises heat-drying an acetone complex of 2-[[4-(3-methoxypropoxy)-3-methylpyridine-2-yl]methylsulfinyl]-1H-benzimidazole sodium salt under reduced pressure.

<8> The method according to any one of the above items <1> to <7>, wherein the heating temperature ranges from 30 to 130° C.

<9> The method according to any one of the above items <1> to <7>, wherein the heating temperature ranges from 100 to 110° C.

<10> The method according to any one of the above items <1> to <9>, wherein the amorphous substance of sulfoxide derivative (I) or the salt thereof has 50 μm or less of average particle diameter and 80 μm or less of 90% cumulative diameter, measured by laser diffractometry.

<11> The method according to any one of the above items <1> to <9>, wherein the amorphous substance of sulfoxide derivative (I) or the salt thereof has 30 μm or less of average particle diameter and 50 μm or less of 90% cumulative diameter, measured by laser diffractometry.

<12> The method according to any one of the above items <1> to <9>, wherein the amorphous substance of sulfoxide derivative (I) or the salt thereof has from 1 to 75 μm of particle diameter, from 5 to 30 μm of average particle diameter and from 10 to 50 μm of 90% cumulative diameter, measured by laser diffractometry.

<13> The method according to any one of the above items <1> to <9>, wherein the amorphous substance of sulfoxide derivative (I) or the salt thereof has from 1 to 50 μm of particle diameter, from 5 to 15 μm of average particle diameter and from 10 to 25 μm of 90% cumulative diameter, measured by laser diffractometry.

<14> The method according to any one of the above items <1> to <9>, wherein the amorphous substance of sulfoxide derivative (I) or the salt thereof has from 1 to 75 μm of particle diameter, measured by laser diffractometry.

<15> The method according to any one of the above items <1> to <9> and <14>, wherein the amorphous substance of sulfoxide derivative (I) or the salt thereof has from 1 to 50 μm of particle diameter, measured by laser diffractometry.

<16> The method according to any one of the above items <1> to <9>, <14> and <15>, wherein the amorphous substance of sulfoxide derivative (I) or the salt thereof has from 5 to 30 μm of average particle diameter, measured by laser diffractometry.

<17> The method according to any one of the above items <1> to <9> and <14> to <16>, wherein the amorphous substance of sulfoxide derivative (I) or the salt thereof has from 5 to 15 μm of average particle diameter, measured by laser diffractometry.

<18> The method according to any one of the above items <1> to <9> and <14> to <17>, wherein the amorphous substance of sulfoxide derivative (I) or the salt thereof has from 10 to 50 μm of 90% cumulative diameter, measured by laser diffractometry.

<19> The method according to any one of the above items <1> to <9> and <14> to <18>, wherein the amorphous substance of sulfoxide derivative (I) or the salt thereof has from 10 to 25 μm of 90% cumulative diameter, measured by laser diffractometry.

<20> An amorphous substance of 2-[[4-(3-methoxypropoxy)-3-methylpyridine-2-yl]methylsulfinyl]-1H-benzimidazole sodium salt, which is obtainable by heat-drying an acetone complex of 2-[[4-(3-methoxypropoxy)-3-methylpyridine-2-yl]methylsulfinyl]-1H-benzimidazole sodium salt or an acetonitrile complex of 2-[[4-(3-methoxypropoxy)-3-methylpyridine-2-yl]-methylsulfinyl]-1H-benzimidazole sodium salt under reduced pressure.

<21> An amorphous substance of 2-[[4-(3-methoxypropoxy)-3-methylpyridine-2-yl]methylsulfinyl]-1H-benzimidazole sodium salt, which is obtained by heat-drying an acetone complex of 2-[[4-(3-methoxypropoxy)-3-methylpyridine-2-yl]methylsulfinyl]-1H-benzimidazole sodium salt or an acetonitrile complex of 2-[[4-(3-methoxypropoxy)-3-methylpyridine-2-yl]-methylsulfinyl]-1H-benzimidazole sodium salt under reduced pressure.

<22> An amorphous substance of 2-[[4-(3-methoxypropoxy)-3-methylpyridine-2-yl]methylsulfinyl]-1H-benzimidazole sodium salt, which is obtainable by heat-drying an acetone complex of 2-[[4-(3-methoxypropoxy)-3-methylpyridine-2-yl]methylsulfinyl]-1H-benzimidazole sodium salt under reduced pressure.

<23> An amorphous substance of 2-[[4-(3-methoxypropoxy)-3-methylpyridine-2-yl]methylsulfinyl]-1H-benzimidazole sodium salt, which is obtained by heat-drying an acetone complex of 2-[[4-(3-methoxypropoxy)-3-methylpyridine-2-yl]methylsulfinyl]-1H-benzimidazole sodium salt under reduced pressure.

<24> The amorphous substance according to the above items <20> to <23>, which has from 1 to 75 μm of particle diameter, from 5 to 30 μm of average particle diameter and from 10 to 50 μm of 90% cumulative diameter, measured by laser diffractometry.

<25> The amorphous substance according to the above items <20> to <23>, which has from 1 to 50 μm of particle diameter, from 5 to 15 μm of average particle diameter and from 10 to 25 μm of 90% cumulative diameter, measured by laser diffractometry.

<26> The amorphous substance according to the above items <20> to <23>, which has from 1 to 75 μm of particle diameter, measured by laser diffractometry.

<27> The amorphous substance according to the above items <20> to <23> and <26>, which has from 1 to 50 μm of particle diameter, measured by laser diffractometry.

<28> The amorphous substance according to the above items <20> to <23>, <26> and <27>, which has from 5 to 30 μm of average particle diameter, measured by laser diffractometry.

<29> The amorphous substance according to the above items <20> to <23> and <26> to <28>, which has from 5 to 15 μm of average particle diameter, measured by laser diffractometry.

<30> The amorphous substance according to the above items <20> to <23> and <26> to <29>, which has from 10 to 50 μm of 90% cumulative diameter, measured by laser diffractometry.

<31> The amorphous substance according to the above items <20> to <23> and <26> to <30>, which has from 10 to 25 μm of 90% cumulative diameter, measured by laser diffractometry.

<32> An acetonitrile complex of 2-[[4-(3-methoxypropoxy)-3-methylpyridine-2-yl]methylsulfinyl]-1H-benzimidazole sodium salt.

BEST MODE FOR CARRYING OUT THE INVENTION

Hereinafter, the present invention will be described in detail.

The term "alkaline metal" used herein concretely means, for example, sodium, potassium, lithium and the like. The term "alkaline earth metal" concretely means, for example, calcium, magnesium and the like. Sodium or magnesium is preferable. Sodium is more preferable.

Furthermore, in the case where "B" represents "½ alkaline earth metal", the salt of sulfoxide derivative is represented by the following formula (II):

(II)

wherein each of $R_1$, $R_2$, $R_3$ and $R_4$ has the same meaning as defined above, and B' represents an alkaline earth metal.

In particular, the sulfoxide derivative (I) or the salt thereof may include, for example, 2-[[4-(3-methoxypropoxy)-3-methylpyridine-2-yl]methylsulfinyl]-1H-benzimidazole disclosed in U.S. Pat. No. 5,045,552 (general designation: Rabeprazole); 2-[[4-(2,2,2-trifluoroethoxy)-3-methylpyridine-2-yl]-methylsulfinyl]-1H-benzimidazole disclosed in U.S. Pat. No. 4,628,098 (general designation: Lansoprazole), 5-methoxy-2-[(4-methoxy-3,5-dimethyl-2-pyridyl)methylsulfinyl]-1H-benzimidazole disclosed in U.S. Pat. No. 4,255,431 (general designation: Omeprazole) or 5-difluoromethoxy-2-[(4,5-dimethoxy-2-pyridyl)methylsulfinyl]-1H-benzimidazole disclosed in U.S. Pat. No. 4,758,579 (general designation: Pantoprazole) and the salts thereof. Each compound can be prepared according to each method disclosed in each of the specification.

The solvated crystal of sulfoxide derivative (I) or the salt thereof may include, for example, the acetone complex (acetone-solvate crystal), the acetonitrile complex (acetonitrile-solvate crystal) or the ethyl acetate complex (ethyl acetate-solvate crystal) of 2-[[4-(3-methoxypropoxy)-3-methylpyridine-2-yl]methylsulfinyl]-1H-benzimidazole, 2-[[4-(2,2,2-trifluoroethoxy)-3-methylpyridine-2-yl]methylsulfinyl]-1H-benzimidazole, 5-methoxy-2-[(4-methoxy-3,5-dimethyl-2-pyridyl)methylsulfinyl]-1H-benzimidazole or 5-difluoromethoxy-2-[(4,5-dimethoxy-2-pyridyl)methylsulfinyl]-1H-benzimidazole, and the acetone complex, the acetonitrile complex or the ethyl acetate complex of the salt thereof.

The acetone complex of 2-[[4-(3-methoxypropoxy)-3-methylpyridine-2-yl]methylsulfinyl]-1H-benzimidazole sodium salt and the acetonitrile complex of 2-[[4-(3-methoxypropoxy)-3-methylpyridine-2-yl]methylsulfinyl]-1H-benzimidazole sodium salt are preferable. The acetone complex of 2-[[4-(3-methoxypropoxy)-3-methylpyridine-2-yl]methylsulfinyl]-1H-benzimidazole sodium salt is more preferable.

The solvated crystal of sulfoxide derivative (I) or the salt thereof is basically obtained by, for example, contacting sulfoxide derivative (I) or the salt thereof with a solvent or dissolving it in a solvent, and then treating the resultant, for example, crystallizing the resultant.

Furthermore, the acetone complex of sulfoxide derivative (I) or the salt thereof is disclosed in U.S. Pat. No. 6,180,652, and, in particular, is represented by the following formula. The complex or the salt thereof can be prepared according to the method disclosed in the specification:

wherein $R_1$ represents a hydrogen atom, a methoxy group or a difluoromethoxy group; $R_2$ represents a methyl group or a methoxy group; $R_3$ represents a 3-methoxypropoxy group, a methoxy group or a 2,2,2-trifluoroethoxy group; $R_4$ represents a hydrogen atom or a methyl group; respectively, m and n each independently represents an integer of 1 to 4, and B represents a hydrogen atom, an alkaline metal or ½ alkaline earth metal.

The acetonitrile complex of sulfoxide derivative (I) or the salt thereof can be prepared by dissolving sulfoxide derivative (I) or the salt thereof in acetonitrile, being left to stand, filtering off the precipitated crystal and drying it.

The acetone complex or acetonitrile complex of sulfoxide derivative (I) or the salt thereof can be used after filtering off without drying in the method of preparing the amorphous substance.

The term "amorphous substance" used herein means an amorphous solid.

The term "moist gas" used herein means gases comprising water and being inert to the sulfoxide derivative (I) or the salt thereof, such as moist air or moist nitrogen. In addition, the moisture content of the moist gas is in the range of from 15 to 60%, preferably from 30 to 40%, in case where the temperature of the moist gas is in the range of from 20 to 35° C.

The term "inert medium" used herein means gas or: liquid being inert to the sulfoxide derivative (I) or the salt thereof. Specific example of the inert gas may include nitrogen gas, argon gas, dried air and the like. The inert liquid may include, but is not limited to, for example, aliphatic hydrocarbons such as 1-heptane and cyclohexene; aromatic hydrocarbons such as toluene; ethers; and the like, as long as 1) the inert, liquid does not dissolve the sulfoxide derivative (I) or the salt thereof and 2) the inert liquid has boiling point of about 60° C. or more.

Hereinafter, the method of preparing the amorphous substance of sulfoxide derivative (I) or the salt thereof according to the present invention, which comprises heat-drying an solvated crystal of the sulfoxide derivative (I) or the salt thereof, will be concretely described.

According to the present invention, the amorphous substance of sulfoxide derivative (I) or the salt thereof can be basically prepared by incorporating an solvated crystal of sulfoxide derivative (I) or the salt thereof into a vibrating vacuum dryer and heat-drying it while, the heat medium is circulated. Preferably, heat-drying is conducted under reduced pressure.

The heat-drying according to the present invention can be conducted with moist gas. In particular, the heat-drying is conducted by removing the solvent from the solvated crystal while the moist gas flows little by little so as to contact with the sulfoxide derivative (I) or the salt thereof at the same time of depressurizing under the heat-vibrating condition. In the drying in which the moisture gas is used, the solvent can be separated by replacing the solvent in the powder with water to facilitate the diffusion migration thereof and promote the evaporation thereof. Accordingly, said drying has an advantage that the heating temperature and depressurizing degree can be decreased by using the moist gas.

The heat-drying according to the present invention can be conducted in an inert medium. In the case where an inert gas is used as the inert medium, the heat-drying is conducted by flowing the inert gas little by little into the reaction container so as to contact with the sulfoxide: derivative (I) or the salt thereof at the same time of heating. In the case where an inert liquid is used as the inert medium, in particular, sulfoxide derivative (I) or the salt thereof is suspended, dispersed in the inert liquid, and heated under the condition with good heat conductance.

While the heating temperature is not limited, the heat-drying can be usually conducted in the range of from 30 to 130° C., preferably from 60 to 120° C., more preferably 100 to 110° C. In addition, the heat-drying time can be usually in the range of from 1 to 160 hour(s), preferably from 3 to 30 hours, although the drying time depends on a drying equipment, heating temperature, degree of depressurization, scale and the like.

The measurement of particle size distribution by laser diffractometry can be conducted, for example, by using "Microtrac X100" (made by Leeds And Northrup). In the case where the particle size distribution of the amorphous substance of sulfoxide derivative (I) or the salt thereof, which is prepared by conducting the above-mentioned heat-drying, is measured by the laser diffractometry, the amorphous substance of sulfoxide derivative (I) or the salt thereof has 50 µm or less, preferably 30 µm or less of average particle diameter, and 80 µm or less, preferably 50 µm or less of 90% cumulative diameter.

In addition, in the case where the particle size distribution of the amorphous substance of sulfoxide derivative (I) or the salt thereof, which is prepared by conducting the above-mentioned heat-drying, is measured by the laser diffractometry, the amorphous substance of sulfoxide derivative (I) or the salt thereof has from 1 to 75 µm of particle diameter, from 5 to 30 µm of average particle diameter and from 10 to 50 µm of 90% cumulative diameter. Preferably, the amorphous substance has from 1 to 50 µm of particle diameter, from 5 to 15 µm of average particle diameter and from 10 to 25 µm of 90% cumulative diameter. The step of making the particle diameter the uniform size can be deleted by obtaining the particles each having the above-mentioned ranges. In addition, since the specific surface of the particles each having relatively small particle diameter can be generally depressed, the particles each having an improved water-resistance property can be obtained.

EXAMPLES

The present invention will be described by way of the following examples which are intended to illustrate, but not limit the present invention.

HPLC Condition for Purity Measurement

Stationary phase: YMC-Pack Pro C18 AS-303 (4.6 mm I.D.× 250 mm, 5 µm);

Mobile phase: MeOH/$H_2$O/AcON$H_4$=550 mL/450 mL/2 g;

Flow rate: 1.0 mL/min;

Temperature: 35° C.; and

Detector: UV 290 nm.

Condition for Measuring Powder X-ray Diffraction Pattern

X-ray: Cu;

Filter: no use;

Voltage: 40 kV;

Current: 20 mA;

Counter monochromator: Curved crystal monochromator;

Diffusing slit: 1 deg;

Scattering slit: 1 deg;

Light accepting slit: 0.15 mm;

Scan speed: 2 deg/min; and

Scanning range: 5 to 0.

Reference Example 1

Preparation of an Acetone Complex of 2-[[4-(3-methoxypropoxy)-3-methylpyridine-2-yl]methyl-sulfinyl]-1H-benzimidazole Sodium Salt The titled compound was prepared according to the method described in U.S. Pat. No. 6,180,652 (Example 7).

Reference Example 2

Preparation of an Amorphous Substance of 2-[[4-(3-methoxypropoxy)-3-methylpyridine-2-yl]methylsulfinyl]-1H-benzimidazole Sodium Salt by Freeze-Dry The titled compound was prepared according to the method described in U.S. Pat. No. 5,045,552 (Example 33).

Example 1

Preparation of an Amorphous Substance of 2-[[4-(3-methoxypropoxy)-3-methylpyridine-2-yl]methylsulfinyl]-1H-benzimidazole Sodium Salt by 110° C./Drying Under Reduced Pressure in 6 kg Scale To a vibrating vacuum dryer (made by CHUO KAKOHKI Co., Ltd., VH-25 type), an acetone complex of 2-[[4-(3-methoxypropoxy)-3-methylpyridine-2-yl]methylsulfinyl]-1H-benzimidazole sodium salt (6 kg: acetone content 26%: 12.35 mol) was placed, and a vibrating vacuum-heating was conducted by circulating a heat medium (80% ethylene glycol/water) heated at 110° C. After heating for 75 minutes, the jacket temperature of the dryer reached at 104° C. (the material temperature: 83° C.). After 5 hours (the jacket temperature: 109° C., the material temperature: 107° C., the degree of vacuum: 0.2 pKa), the drying was stopped and then, the amorphous substance of 2-[[4-(3-methoxypropoxy)-3-methylpyridine-2-yl]methylsulfinyl]-1H-benzimidazole sodium salt (4.66 kg, acetone: 260 ppm, HPLC purity: 99.6%) was obtained. The powder X-ray diffraction pattern of the resulting amorphous substance was consistent with that of the freeze-dried product.

Example 2

Preparation of an Amorphous Substance of 2-[[4-(3-methoxpropoxy)-3-methylpyridine-2-yl]methylsulfinyl]-1H-benzimidazole Sodium Salt by 105° C./Drying Under Reduced Pressure in 6 kg Scale To a vibrating vacuum dryer (made by CHUO KAKOHKI Co., Ltd., VH-25 type), an acetone complex of 2-[[4-(3-methoxypropoxy)-3-methylpyridine-2-yl]methylsulfinyl]-1H-benzimidazole sodium salt (6 kg: acetone content 26%: 12.35 mol) was placed, and a vibrating vacuum-heating was conducted by circulating a heat medium (80% ethylene glycol/water) heated at 105° C. After heating for 2 hours, the jacket temperature of the dryer reached at 103° C. (the material temperature: 75° C., the degree of vacuum: 0.2 pKa). After 7 hours, the drying was stopped and then, the amorphous substance of 2-[[4-(3-methoxypropoxy)-3-methylpyridine-2-yl]-methylsulfinyl]-1H-benzimidazole sodium salt (4.57 kg, acetone: 280 ppm, HPLC purity: 99.6%) was obtained. The powder X-ray diffraction pattern of the resulting amorphous substance was consistent with that of the freeze-dried product.

Example 3

Preparation of an Amorphous Substance of 2-[[4-(3-methoxypropoxy)-3-methylpyridine-2-yl]methylsulfinyl]-1H-benzimidazole Sodium Salt by 100° C./Drying Under Reduced Pressure in 6 kg Scale To a vibrating vacuum dryer (made by CHUO KAKOHKI Co., Ltd., VH-25 type), an acetone complex of 2-[[4-(3-methoxypropoxy)-3-methylpyridine-2-yl]methylsulfinyl]-1H-benzimidazole sodium salt (6 kg: acetone content 26%: 12.35 mol) was placed, and a vibrating vacuum-heating was conducted for 3 hours by circulating a heat medium (80% ethylene glycol/water) heated at 60° C. Then, a vibrating vacuum-heating was conducted by circulating a heat medium (80% ethylene glycol/water) heated at 100° C. After heating for 1 hour and 40 minutes, the jacket temperature of the dryer reached at 88° C. (the material temperature: 69° C., the degree of vacuum: 0.2 pKa). After 14 hours, the drying was stopped and then, the amorphous substance of 2-[[4-(3-methoxypropoxy)-3-methylpyridine-2-yl]-methylsulfinyl]-1H-benzimidazole sodium salt (4.54 kg, acetone: 290 ppm, HPLC purity: 99.6%) was obtained. The powder X-ray diffraction pattern of the resulting amorphous substance was consistent with that of the freeze-dried product.

Example 4

Preparation of an Amorphous Substance of 2-[[4-(3-methoxypropoxy)-3-methylpyridine-2-yl]methylsulfinyl]-1H-benzimidazole Sodium Salt by 120° C./Drying Under Reduced Pressure in 50 g Scale To a 300 mL eggplant type flask, an acetone complex of 2-[[4-(3-methoxypropoxy)-3-methylpyridine-2-yl]methylsuffinyl]-1H-benzimidazole sodium salt (50 g: acetone content 12%: 122 mmol) was placed, and a heat-drying under reduced pressure was conducted for 2 hours by a vacuum pump and an evaporator while conducting an intermittent rotation in oil bath heated at 60° C. Then, a heat-drying under reduced pressure (the degree of vacuum: 0.2 pKa) was conducted by evaporator while conducting an intermittent rotating in oil bath heated at 120° C. After 1 hour, the drying was stopped and then, the amorphous substance of 2-[[4-(3-methoxypropoxy)-3-methylpyridine-2-yl]methylsuffinyl]-1H-benzimidazole sodium salt (acetone: 80 ppm, HPLC purity: 99.6%) was obtained. The powder X-ray diffraction pattern of the resulting amorphous substance was consistent with that of the freeze-dried-product.

Example 5

Preparation of an Amorphous Substance of 2-[[4-(3-methoxypropoxy)-3-methylpyridine-2-yl]methylsulfinyl]-1H-benzimidazole Sodium Salt by 115° C./Drying Under Reduced Pressure in 50 g Scale To a 300 mL eggplant type flask, an acetone complex of 2-[[4-(3-methoxypropoxy)-3-methylpyridine-2-yl]methylsulfinyl]-1H-benzimidazole sodium salt (50 g: acetone content 12%: 122 mmol) was placed, and a heat-drying under reduced pressure was conducted for 2 hours by a vacuum pump and an evaporator while conducting intermittent rotation in oil bath heated at 60° C. Then, a heat-drying under reduced pressure (the degree of vacuum: 0.2 pKa) was conducted by an evaporator while conducting an intermittent rotation in oil bath heated at 115° C. After heating for 2 hours, the drying was stopped and then, the amorphous substance of 2-[[4-(3-methoxypropoxy)-3-methylpyridine-2-yl]methylsulfinyl]-1H-benzimidazole sodium salt (acetone: 240 ppm, HPLC purity: 99.6%) was obtained. The powder X-ray diffraction pattern of the resulting amorphous substance was consistent with that of the freeze-dried product.

Example 6

Preparation of an Amorphous Substance of 2-[[4-(3-methoxypropoxy)-3-methylpyridine-2-yl]-methyl-sufinyl]-1H-benzimidazole Sodium Salt by 105° C./Drying Under Reduced Pressure in 50 g Scale To a 300 mL eggplant type flask, an acetone complex of 2-[[4-(3-methoxypropoxy)-3-methylpyridine-2-yl]methylsulfinyl]-1H-benzimidazole sodium salt (50 g: acetone content 10%: 125 mmol) was placed, and a heat-drying under reduced pressure was conducted for 2 hours by a vacuum pump and an evaporator while conducting an intermittent rotation in oil bath heated at 60° C. Then, a heat-drying under reduced pressure (the material temperature: 100° C., the degree of vacuum: 0.2 pKa) was conducted by an evaporator while conducting an intermittent rotation in oil bath heated at 105° C. After heating for 5 hours, the drying was stopped and then, the amorphous substance of 2-[[4-(3-methoxypropoxy)-3-methylpyridine-2-yl]-methylsulfinyl]-1H-benzimidazole sodium salt (acetone: 190 ppm, HPLC purity: 99.6%) was obtained. The powder X-ray diffraction pattern of the resulting amorphous substance was consistent with that of the freeze-dried product.

Example 7

Preparation of an Amorphous Substance of 2-[[4-(3-methoxypropoxy)-3-methylpyridine-2-yl]methyl-sulfinyl]-1H-benzimidazole Sodium Salt by 82° C./Drying Under Reduced Pressure in 1 kg Scale To a vibrating vacuum dryer (made by CHUO KAKOHKI Co., Ltd., VU-15 type), an acetone complex of 2-[[4-(3-methoxypropoxy)-3-methylpyridine-2-yl]methylsulfinyl]-1H-benzimidazole sodium salt (1 kg: acetone content 10%: 2.5 mol) was placed, and a vibrating vacuum-heating (the degree of vacuum: <0.2 pKa) was conducted by circulating hot water heated at 82° C. After 137 hours, the drying was stopped and then, the amorphous substance of 2-[[4-(3-methoxypropoxy)-3-methylpyridine-2-yl]methylsulfinyl]-1H-benzimidazole sodium salt (acetone: 1870 ppm) was obtained.

Example 8

Preparation of an Amorphous Substance of 2-[[4-(3-methoxypyroxy)-3-methylpyridine-2-yl]methylsulfinyl]-1H-benzimidazole Sodium Salt by 80° C./Drying Under Reduced Pressure in 15 g Scale To a tray-type vacuum dryer, an acetone complex of 2-[[4-(3-methoxypropoxy)-3-methylpyridine-2-yl]methylsulfinyl]-1H-benzimidazole sodium salt (15 g: acetone content 10%: 38 mmol) was placed, and a drying under reduced pressure was conducted at 80° C. (the degree of vacuum: <0.2 pKa). After heating for 15 hours, the drying was stopped and then, the amorphous substance of 2-[[4-(3-methoxypropoxy)-3-methylpyridine-2-yl]methylsulfinyl]-1H-benzimidazole sodium salt (13 g, acetone: 130 ppm, HPLC purity: 99.6%) was obtained. The powder X-ray diffraction pattern of the resulting amorphous substance was consistent with that of the freeze-dried product.

Example 9

Preparation of an Amorphous Substance of 2-[[4-(3-methoxypropoxy)-3-methylpyridine-2-yl]methyl-sulfinyl]-1H-benzimidazole Sodium Salt by 105° C./Drying Under Reduced Pressure in 12 kg Scale To a vibrating vacuum dryer (made by CHUO, KAKOHKI Co., Ltd., VH-25 type), an acetone complex of 2-[[4-(3-methoxypropoxy)-3-methylpyridine-2-yl]methylsulfinyl]-1H-benzimidazole sodium salt (11.5 kg: acetone content 17%: 25.0 mol) was placed, and a vibrating vacuum-heating (the degree of vacuum: 0.2 pKa) was conducted by circulating a heat medium (80% ethylene glycol/water) heated at 105° C. After 15 hours from the time of reaching the jacket temperature at 100° C. or more, the drying was stopped and then, the amorphous substance of 2-[[4-(3-methoxypropoxy)-3-methylpyridine-2-yl]methylsulfinyl]-1H-benzimidazole sodium salt (9.4 kg, acetone: 130 ppm, HPLC purity: 99.3%) was obtained. The powder X-ray diffraction pattern of the resulting amorphous substance was consistent with that of the freeze-dried product.

Example 10

Preparation of an Amorphous Substance of 2-[[4-(3-methoxypropoxy)-3-methylpyridine-2-yl]methyl-sulfinyl]-1H-benzimidazole Sodium Salt by 60° C./Moist Drying Under Reduced Pressure in 10 kg Scale To a vibrating vacuum dryer (made by CHUO KAKOBKI Co., Ltd., VU-15 type), an acetone complex of 2-[[4-(3-methoxypropoxy)-3-methylpyridine-2-yl]methylsulfinyl]-1H-benzimidazole sodium salt (10.2 kg: acetone content about 24%: 26.7 mol) was placed, and a vibrating vacuum-heating was conducted by circulating hot water for 1 hour at 30° C. and then, for 1 hour at 40° C. and then, for 30 minutes at 50° C. Then, hot water heated at 60° C. was circulated, and nitrogen gas flowed little by little to control the degree of vacuum to 13 mmHg. Further, drying was conducted for 67 hours. Then, while atmospheric air (room temperature: 22 to 27° C., humidity: 16 to 60%, air flow rate: 10 to 13 m³/hr) flowed little by little (13 mmHg), and further, drying was conducted at 60° C. for 84 hours. After 152 hours, the drying was stopped and then, the amorphous substance of 2-[[4-(3-methoxypropoxy)-3-methylpyridine-2-yl]methylsulfinyl]-1H-benzimidazole sodium salt (acetone: 340 ppm) was obtained.

Example 11

Preparation of an Amorphous Substance of 2-[[4-(3-methoxypropoxy)-3-methylpyridine-2-yl]methyl-sulfinyl]-1H-benzimidazole Sodium Salt by 60° C./Moist Drying Under Reduced Pressure in 9 kg Scale To a vibrating vacuum dryer (made by CHUO KAKOHKI Co., Ltd., VU-15 type), an acetone complex of 2-[[4-(3-methoxypropoxy)-3-methylpyridine-2-yl]methylsulfinyl]-1H-benzimidazole sodium salt (9.1 kg: acetone content about 20%: 19.1 mol) was placed. Hot water was circulated at 20°

C. for 2 hours, then at 30° C., and while atmospheric air (room temperature: 26 to 32° C., humidity: 30 to 40%, air flow rate: 10 to 13 m³/hr) flowed little by little (650 mmHg), drying was conducted for 67 hours. Further, leak was stopped and drying under reduced pressure was conducted for 48 hours (for 24 hours at 30° C., and for 24 hours at 50° C.). The amorphous substance of 2-[[4-(3-methoxypropoxy)-3-methylpyridine-2-yl]-methylsulfinyl]-1H-benzimidazole sodium salt (2.1 kg, acetone: 600 ppm, HPLC purity: 99.8%) was obtained.

Example 12

Preparation of an Amorphous Substance of 2-[[4-(3-methoxypropoxy)-3-methylpyridine-2-yl]methyl-sulfinyl]-1H-benzimidazole Sodium Salt by 60° C./Moist Drying Under Reduced Pressure in 3 kg Scale To a vibrating vacuum dryer (made by CHUO KAKOHKI Co., Ltd., VU-15 type), an acetone complex of 2-[[4-(3-methoxypropoxy)-3-methylpyridine-2-yl]methylsulfinyl]-1H-benzimidazole sodium salt (2.5 kg: acetone content about 24%: 6.6 mol) was placed, hot water heated at 60° C. was circulated, and while atmospheric air (room temperature: 27 to 32° C., humidity: 30 to 40%, air flow rate: 0.68 to 1.25 L/min) flowed little by little (4 mmHg), drying was conducted for 92 hours. The amorphous substance of 2-[[4-(3-methoxypropoxy)-3-methylpyridine-2-yl]methylsulfinyl]-1H-benzimid azole sodium salt (2.0 kg, acetone: 1600 ppm) was obtained.

Example 13

Preparation of an Amorphous Substance of 2-[[4-(3-methoxypropoxy)-3-methylpyridine-2-yl]methyl-sulfinyl]-1H-benzimidazole Sodium Salt by 30° C./Drying Under Reduced Pressure and Moist Condition in 3 kg Scale To a vibrating vacuum dryer (made by CHUO KAKOHKI Co., Ltd., VUA-20 type), an acetone complex of 2-[[4-(3-methoxypropoxy)-3-methylpyridine-2-yl]methylsulfinyl]-1H-benzimidazole sodium salt (2.5 kg: acetone content about 15%: 5.5 mol) was placed. Hot water heated at 30° C. was circulated, moist nitrogen flowed little by little to control the degree of vacuum to 13 mmHg, and drying was conducted for 21 hours (room temperature: 30° C., humidity: 40%, moist nitrogen flow rate: 207 m³/hr). The amorphous substance of 2-[[4-(3-methoxypropoxy)-3-methylpyridine-2-yl]methyl-sulfinyl]-1H-benzimidazole sodium salt (acetone: 510 ppm) was obtained.

Example 14

Preparation of an Amorphous Substance of 2-[[4-(3-methoxypropoxy)-3-methylpyridine-2-yl]methyl-sulfinyl]-1H-benzimidazole Sodium Salt by 50° C./Moist Drying with Air Supply in 10 g Scale In a box-type air supply-dryer, an acetone complex of 2-[[4-(3-methoxypropoxy)-3-methylpyridine-2-yl]methyl-sulfinyl]-1H-benzimidazole sodium salt (10 g: acetone content about 12%: 23 mmol) was placed in petri dish. The temperature of the dryer was set at 50° C., and air supply-drying was conducted for 48 hours (humidity in the room: 50%). The amorphous substance of 2-[[4-(3-methoxypropoxy)-3-methylpyridine-2-yl]methylsulfinyl]-1H-benzimidazole sodium salt (9.0 g, acetone: 40 ppm, HPLC purity: 99.8%) was obtained. The powder X-ray diffraction pattern of the resulting amorphous substance was consistent with that of the freeze-dried product.

Figure 1:
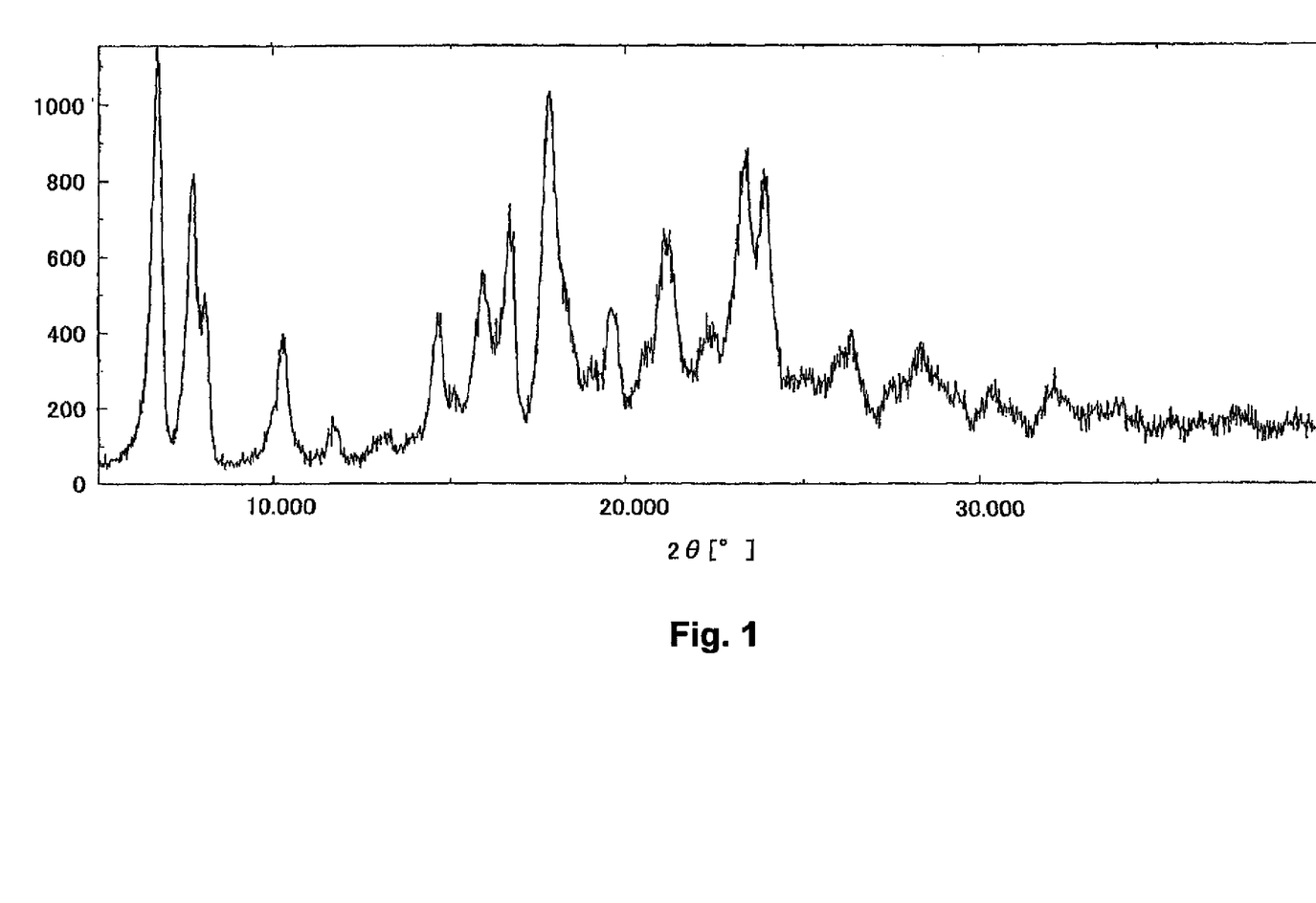
FIG. 1 is a graph showing powder X-ray diffraction pattern as for an acetone complex of 2-[[4-(3-methoxypropoxy)-3-methylpyridine-2-yl]-methylsulfinyl]-1H-benzimidazole sodium salt.
Figure 2:
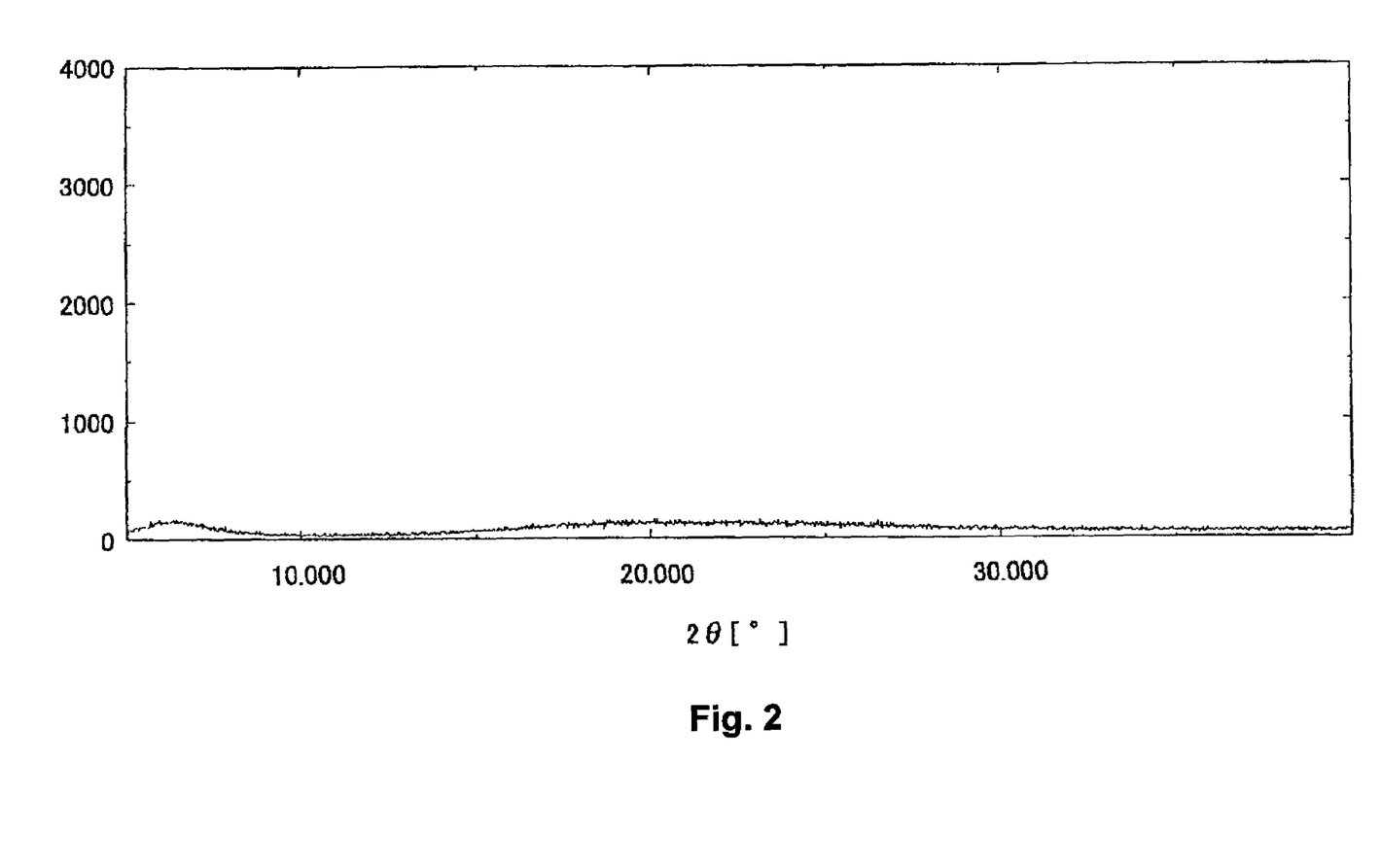
FIG. 2 is a graph showing powder X-ray diffraction pattern as for the freeze-dried product (Reference Example 2).
Figure 3:
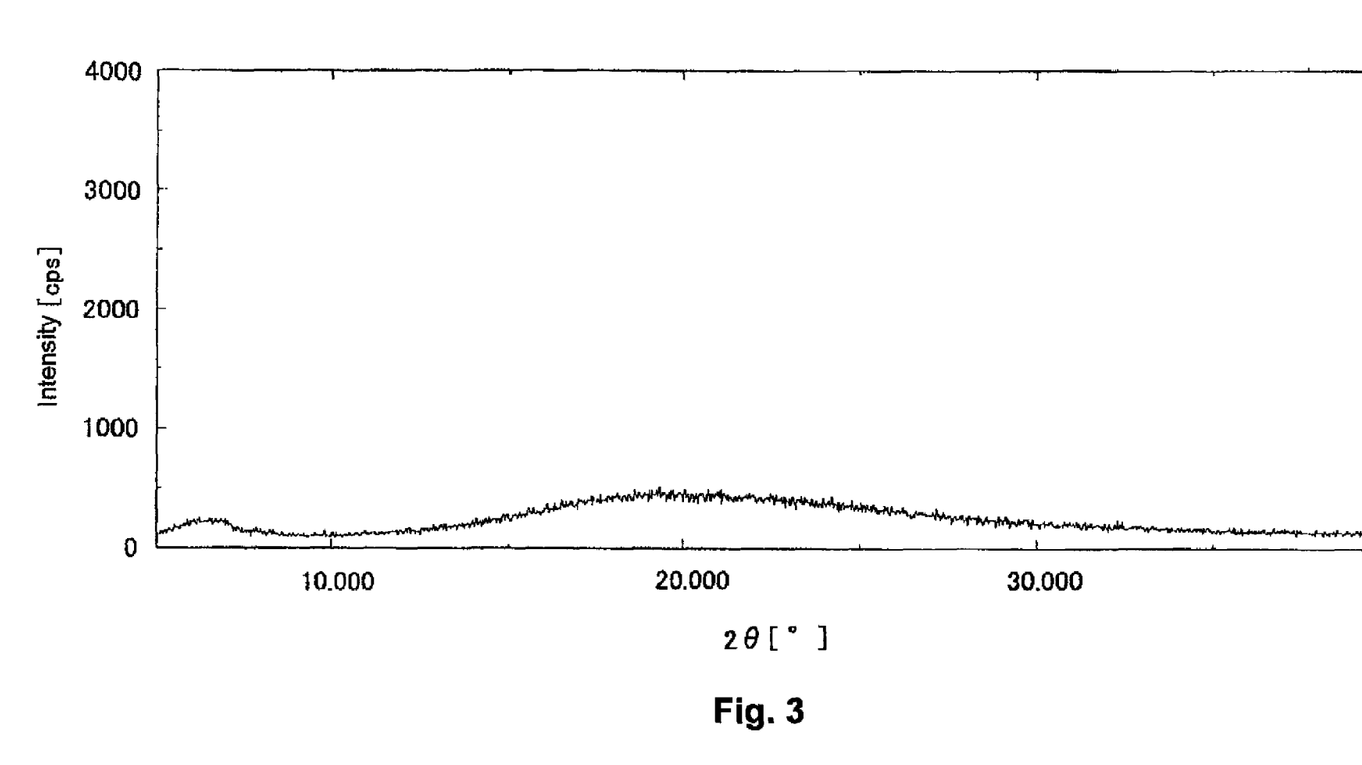
FIG. 3 is a graph showing powder X-ray diffraction pattern as for the heat-dried product (Example 1).

FIG. 1 shows a powder X-ray diffraction pattern as for an acetone complex of 2-[[4-(3-methoxypropoxy)-3-methylpy-ridine-2-yl]methylsulfinyl]-1H-benzimidazole sodium salt; FIG. 2 shows a powder X-ray diffraction pattern as for the freeze-dried product (Reference Example 2); and FIG. 3 shows a powder X-ray diffraction pattern as for the heat-dried product (Example 1), respectively.

Example 15

Figure 7:
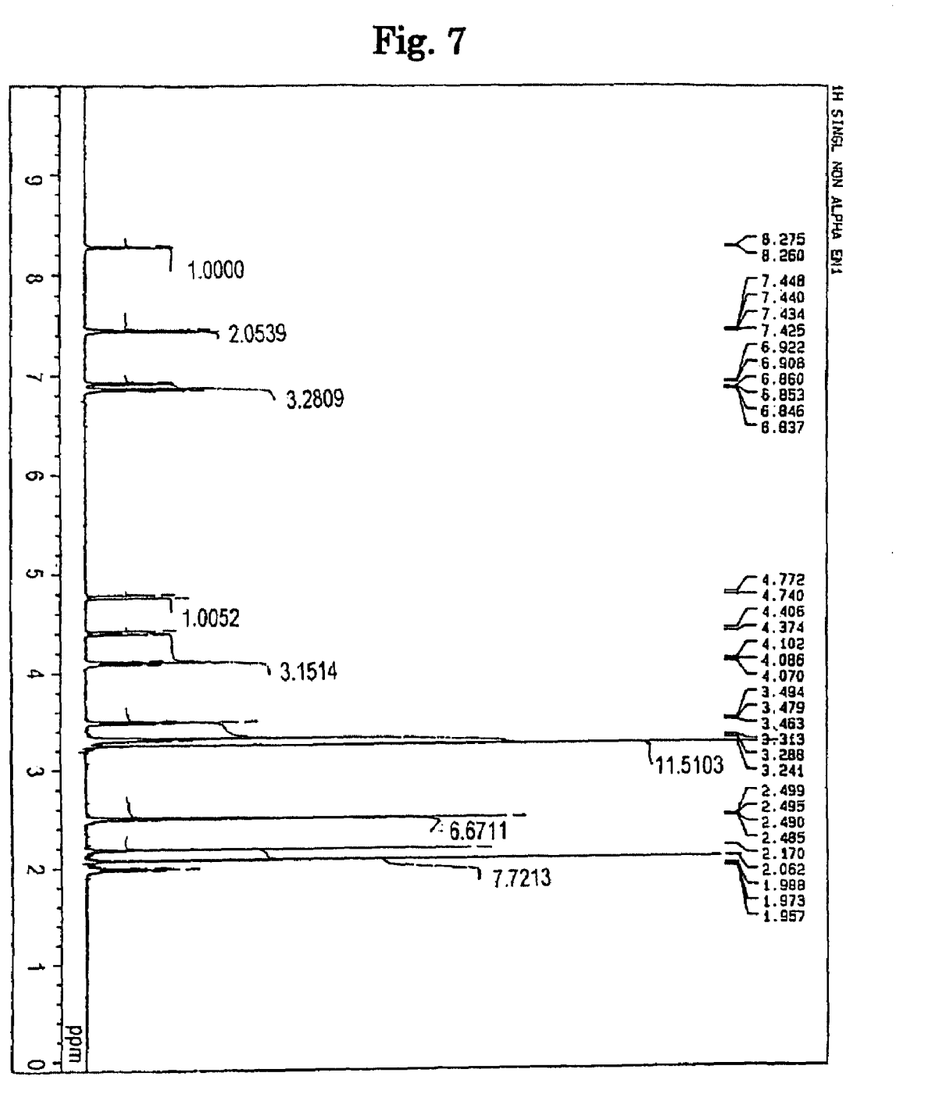
FIG. 7 is a graph showing $^1$H-NMR chart as for the acetonitrile complex of 2-[[4-(3-methoxypropoxy)-3-methylpyridine-2-yl]methylsulfinyl]-1H-benzimidazole sodium salt.
Figure 8:
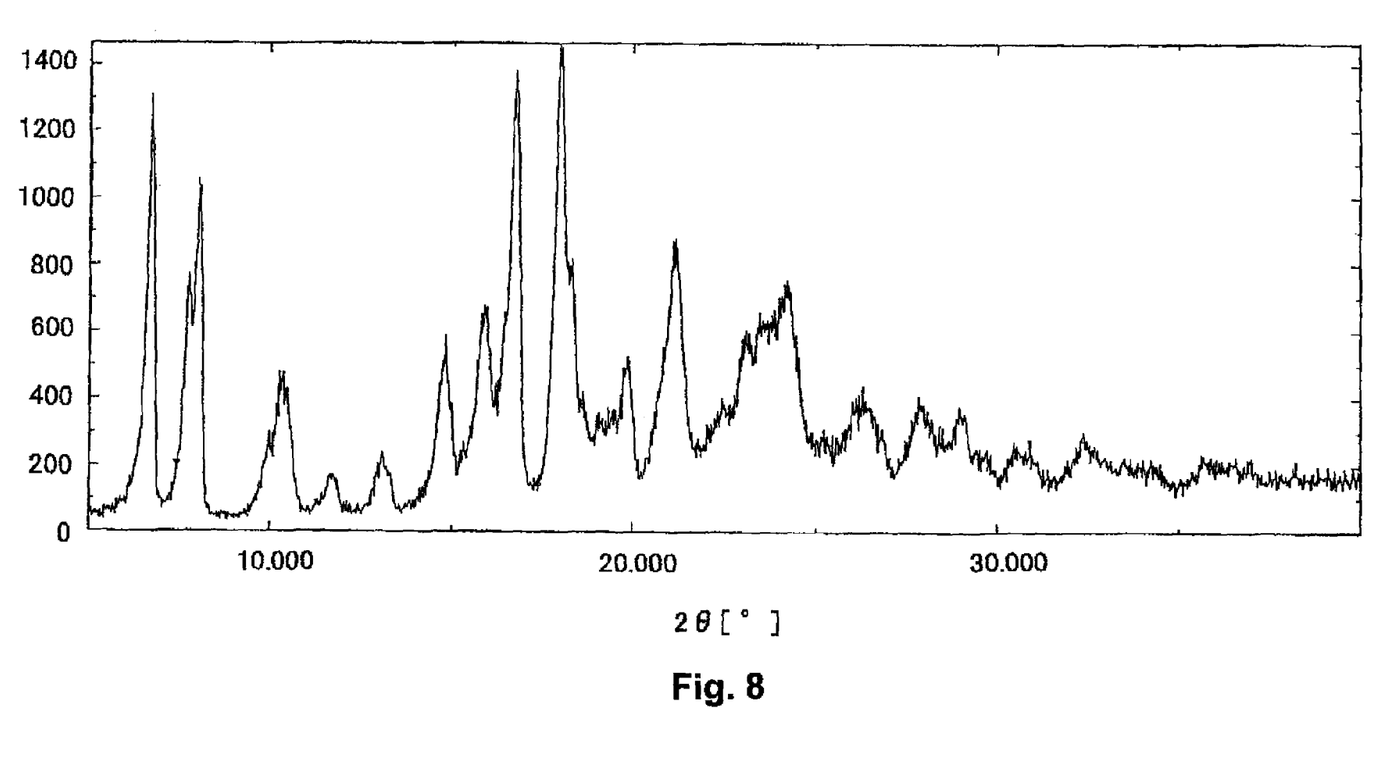
FIG. 8 is a graph showing powder X-ray diffraction pattern as for the acetonitrile complex of 2-[[4-(3-methoxypropoxy)-3-methylpyridine-2-yl]-methylsulfinyl]-1H-benzimidazole sodium salt.

Preparation of an Acetonitrile Complex of 2-[[4-(3-methoxypropoxy)-3-methylpyridine-2-yl]methyl-sulfinyl]-1H-benzimidazole Sodium Salt 10.0 g of 2-[[4-(3-methoxypropoxy)-3-methylpyridine-2-yl]-methylsulfinyl]-1H-benzimidazole sodium salt was dissolved in 20 ml of acetonitrile and then, was left to stand at 22° C. for 18 hours. The precipitated crystal was filtered off, washed with 30 ml of acetonitrile, and dried under reduced pressure for 2 hours, to obtain 9.1 g of a colorless acetonitrile complex of 2-[[4-(3-methoxypropoxy)-3-methylpyridine-2-yl]-methylsulfinyl]-1H-benzimidazole sodium salt (acetonitrile: 8.4%). The powder X-ray diffraction pattern as for the resulting acetone complex denotes crystal structure. Furthermore, FIG. 7 shows a $^1$H-NMR chart as for the acetonitrile complex; FIG. 8 shows a powder X-ray diffraction pattern as for the acetonitrile complex; and Table 1 shows diffraction angle and relative intensity in the powder X-ray diffraction pattern as for the acetonitrile complex; respectively.

$^1$H-NMR (400 MHz, DMSO-$d_6$)

δ: 1.97 (quintet, J=6 Hz, 2H) 2.17 (s, 3H) 3.24 (s, 3H) 3.48 (t, J=6 Hz, 2H) 4.09 (t, J=6 Hz, 2H) 4.39 (d, J=13 Hz, 1H) 4.76 (d, J=13 Hz, 1H) 6.85 (m, 2H) 6.92 (d, J=6 Hz, 1H) 7.44 (m, 2H) 8.27 (d, J=6 Hz, 1H).

TABLE 1

| Diffraction angle (2θ, °) | Relative intensity (I/I$_0$) |
|---|---|
| 6.74 | 89 |
| 7.76 | 51 |
| 8.08 | 74 |
| 9.98 | 22 |
| 10.36 | 32 |
| 10.48 | 29 |
| 14.74 | 35 |
| 14.80 | 37 |
| 15.80 | 43 |
| 15.90 | 45 |
| 16.76 | 97 |
| 17.98 | 100 |
| 18.30 | 55 |
| 18.60 | 29 |
| 19.46 | 23 |
| 19.80 | 35 |
| 19.86 | 38 |
| 21.16 | 57 |
| 22.48 | 27 |
| 23.08 | 41 |
| 23.44 | 43 |
| 23.84 | 45 |
| 24.24 | 50 |
| 26.28 | 31 |
| 26.62 | 25 |
| 27.86 | 27 |
| 28.20 | 25 |

TABLE 1-continued

| Diffraction angle (2θ, °) | Relative intensity (I/I₀) |
|---|---|
| 28.96 | 25 |
| 29.12 | 25 |

Example 16

Figure 9:
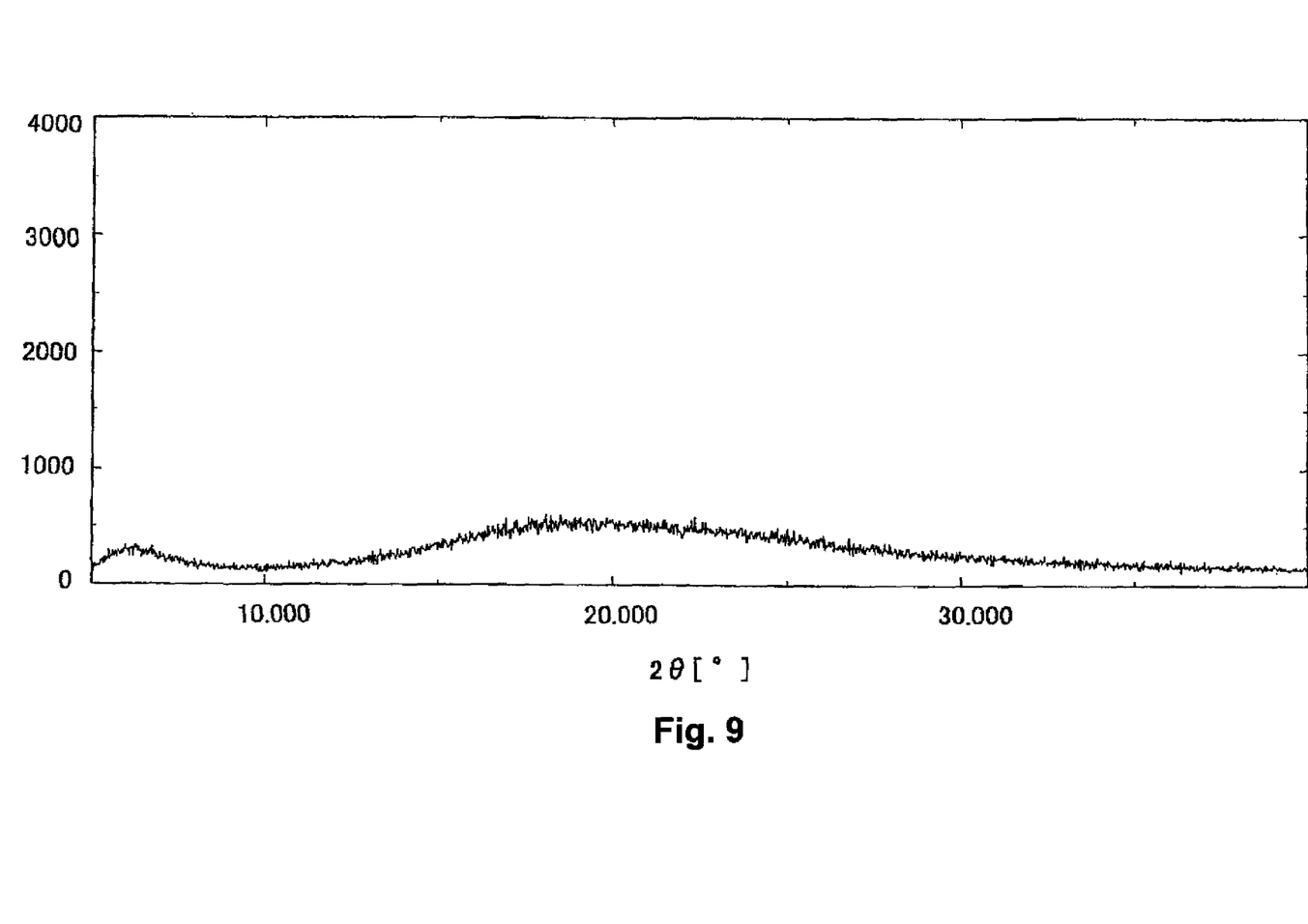
FIG. 9 is a graph showing powder X-ray diffraction pattern as for the heat-dried product (Example 16).

Preparation of an Amorphous Substance of 2-[[4-(3-methoxypropoxy)-3-methylpyridine-2-yl]methyl-sulfinyl]-1H-benzimidazole Sodium Salt by 105° C./Drying Under Reduced Pressure in 5 g Scale To a tray-type vacuum dryer, an acetonitrile complex of 2-[[4-(3-methoxypropoxy)-3-methylpyridine-2-yl]methyl-sulfinyl]-1H-benzimidazole sodium salt (10 g, acetone content: 8.4%, 38 mmol) was placed, and dried under reduced pressure at 105° C. by a vacuum pump (the degree of vacuum: 0.2 pKa). After heating for 5 hours, the drying was stopped. The amorphous substance of 2-[[4-(3-methoxypropoxy)-3-methylpyridine-2-yl]-methylsulfinyl]-1H-benzimidazole sodium salt (4 g, acetonitrile: 4 ppm, HPLC purity: 99.7%) was obtained. The powder X-ray diffraction pattern of the resulting amorphous substance was consistent with that of the freeze-dried product. Furthermore, FIG. 9 shows a powder X-ray diffraction pattern as for the heat-dried product (Example 16).

Figure 4:
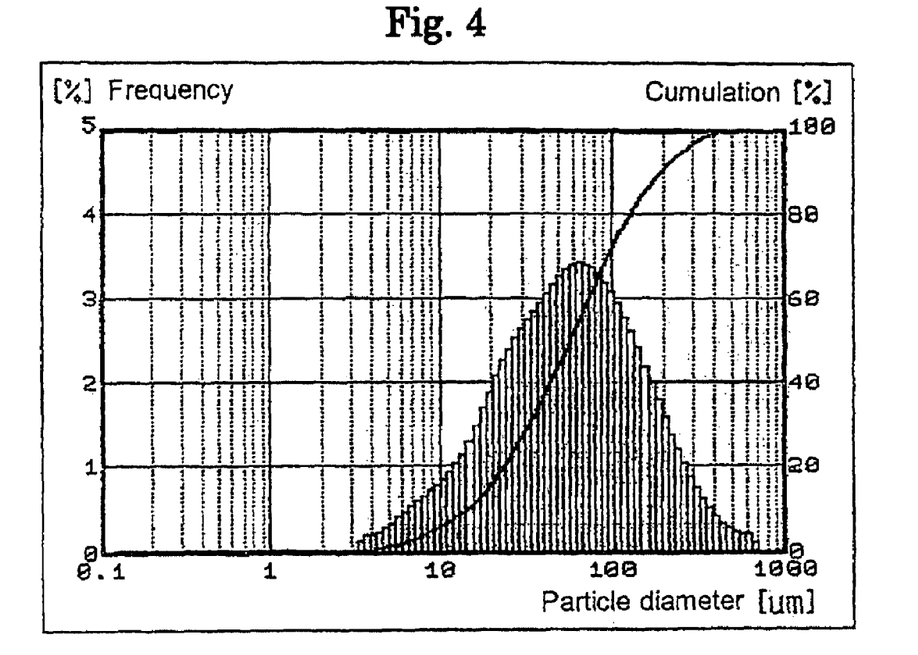
FIG. 4 is a graph showing particle size distribution as for the freeze-dried product (Reference Example 2).
Figure 5:
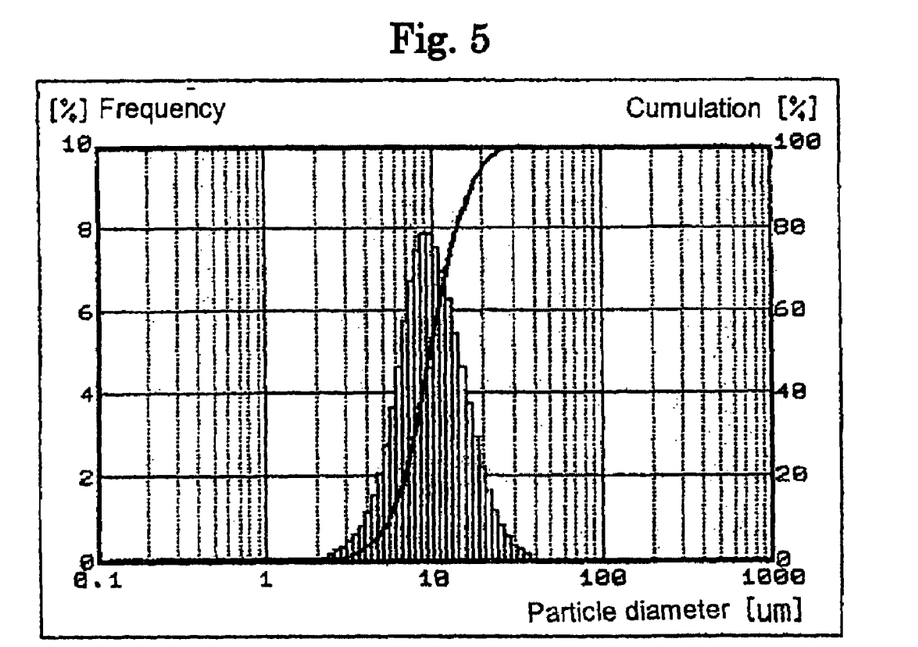
FIG. 5 is a graph showing particle size distribution as for the heat-dried product (Example 3).

Measurement of Particle Size Distribution:

As for each of amorphous substances of 2-[[4-(3-methoxypropoxy)-3-methylpyridine-2-yl]methylsulfinyl]-1H-benzimidazole sodium salt obtained by freeze-drying (Reference example 2), heat-drying (Example 3), respectively, the particle size distributions were measured by "Microtrac X100" (prepared by Leeds And Northrup). FIG. 4 shows the result of the freeze-dried product, and FIG. 5 shows the result of the heat-dried product.

While the particle size distribution of the freeze-dried product was broad, that of the heat-dried product was sharp. Thus, the heat-drying could provide an amorphous-substance having high uniformity.

Measurement of Specific Surface:

As for each of amorphous substances of 2-[[4-(3-methoxypropoxy)-3-methylpyridine-2-yl]methylsulfinyl]-1H-benzimidazole sodium salt obtained by freeze-drying (Reference example 2), heat-drying (Example 3), respectively, the nitrogen-absorption isotherms were measured at liquid nitrogen temperature (77 K) by a high accuracy full automatic gas absorption equipment "BELSORP 36" (prepared by Japan Bell) after vacuum degassing at 50° C. These isotherms were analyzed by BET method to obtain the specific surface. The following Table 2 shows the specific surface and 90% cumulative diameter calculated by measurement of the particle size distribution, as for the freeze-dried product and the heat-dried product.

TABLE 2

| | Specific surface | | 90% cumulative diameter (μm) |
|---|---|---|---|
| | m²/g | Relative comparison | |
| The freeze-dried product | 2.3 | 1.00 | 192.3 |
| The heat-dried product | 1.6 | 0.70 | 18.0 |

It was found that the particle diameter and the specific surface of the heat-dried product were smaller than those of the freeze-dried product. Accordingly, it is believed that the heat-dried product has the water resistance superior to the freeze-dried product.

Measurement of Thermal Analysis:

As for the acetone complex of 2-[[4-(3-methoxypropoxy)-3-methylpyridine-2-yl]methylsulfinyl]-1H-benzimidazole sodium salt, the thermal analysis (IG-DTA) was conducted under the following conditions:

Reference: $Al_2O_3$;

Scan speed: 2° C./min;

Upper limit temperature: 120° C.; and

Lower limit temperature: 20° C.

Figure 6:
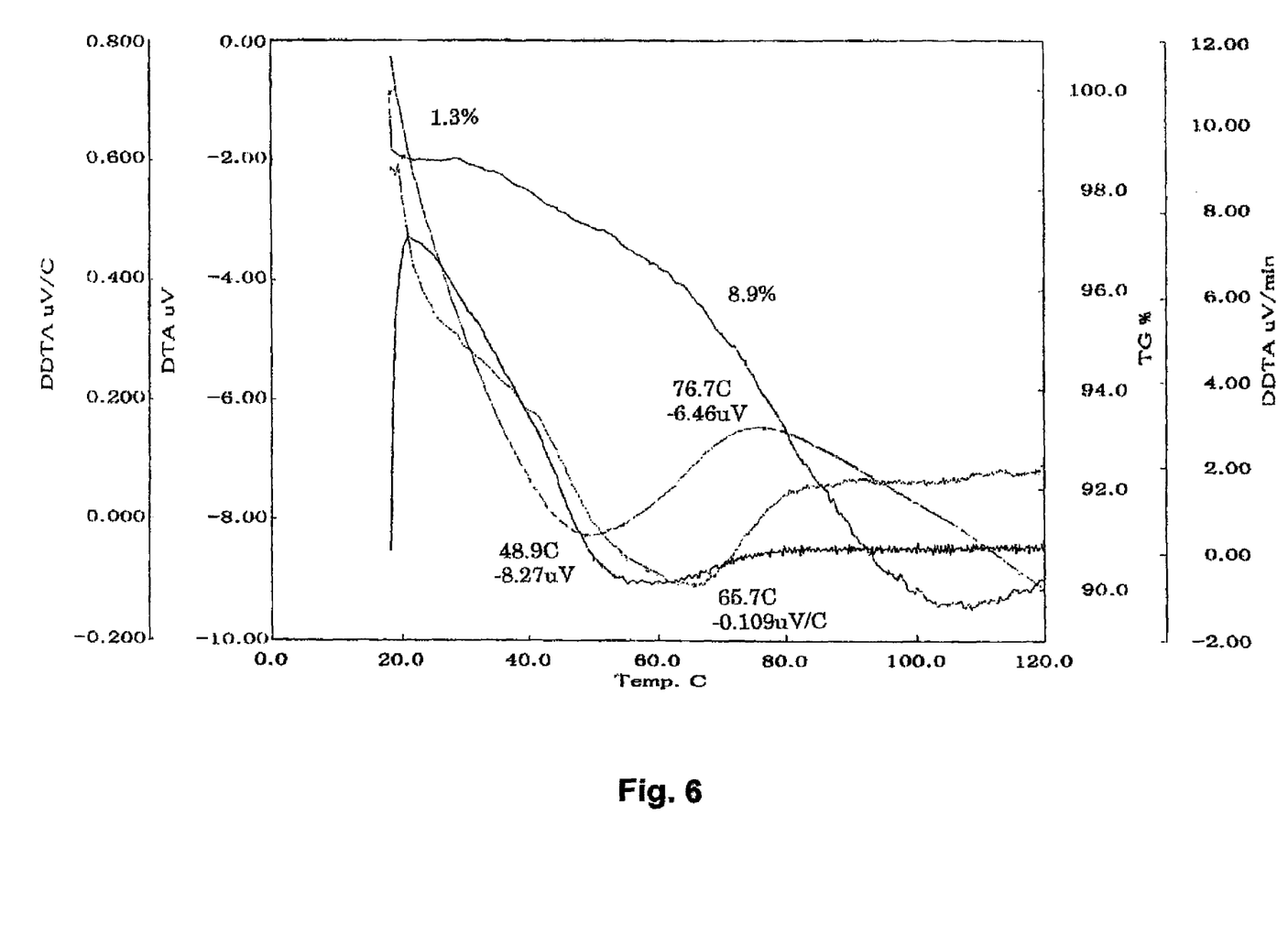
FIG. 6 is a graph showing the result of thermal analysis as for the acetone complex of 2-[[4-(3-methoxypropoxy)-3-methylpyridine-2-yl]-methylsulfinyl]-1H-benzimidazole sodium salt.

FIG. 6 shows the result of the thermal analysis.

The measurement result shows that at the temperature of 65.7° C. or more, the weight of the acetone complex of 2-[[4-(3-methoxypropoxy)-3-methylpyridine-2-yl]methyl-sulfinyl]-1H-benzimidazole sodium salt starts to be decreased, and that at the temperature of 76.7° C. or more, the acetone starts to be effectively decreased.

INDUSTRIAL APPLICABILITY

The heat-drying method according to the present invention enables to stably obtain the amorphous substance of sulfoxide derivative (I) or the salt thereof in industrial scale from the solvated crystal of sulfoxide derivative (I) or the salt thereof. Further, the drying method according to the present invention can make the particle size of the amorphous substance of sulfoxide derivative (I) or the salt thereof the same or similar size. Accordingly, the drying method according to the present invention, by comparison of the prior freeze-dry method, reduces the steps at the same time of greatly reducing the cost including time and energy, furthermore is believed to be preferred in light of environmental protection.

What is claimed is:

1. A method of preparing an amorphous substance of 2-[[4-(3-methoxypropoxy)-3-methylpyridine-2-yl]methylsulfi-nyl]-1H-benzimidazole sodium salt, which comprises heat-drying an acetone complex of 2-[[4-(3-methoxypropoxy)-3-methylpyridine-2-yl]methylsulfinyl]-1H-benzimidazole sodium salt under reduced pressure to obtain said amorphous substance of 2-[[4-(3-methoxypropoxy)-3-methylpyridine-2-yl]methylsulfinyl]-1H-benzimidazole sodium salt.

2. The method according to claim 1, wherein the acetone complex is heat-dried with moist gas.

3. The method according to claim 1, wherein the acetone complex is heat-dried in an inert medium.

4. The method according to claim 1, wherein the heating temperature ranges from 30 to 130° C.

5. The method according to claim 1, wherein the heating temperature ranges from 100 to 110° C.

6. The method according to claim 1, wherein the amorphous substance of 2-[[4-(3-methoxypropoxy)-3-methylpyridine-2-yl]methylsulfinyl]-1H-benzimidazole sodium salt has 50 μm or less of average particle diameter and 80 μm or less of 90% cumulative diameter, measured by laser diffractometry.

7. The method according to claim 1, wherein the amorphous substance of 2-[[4-(3-methoxypropoxy)-3-methylpyridine-2-yl]methylsulfinyl]-1H-benzimidazole sodium salt has 30 μm or less of average particle diameter and 50 μm or less of 90% cumulative diameter, measured by laser diffractometry.

* * * * *